United States Patent [19]

Chang

[11] 4,358,951
[45] Nov. 16, 1982

[54] ZINC OXIDE THIN FILM SENSOR HAVING IMPROVED REDUCING GAS SENSITIVITY

[75] Inventor: Shih-Chia Chang, Troy, Mich.

[73] Assignee: General Motors Corporation, Detroit, Mich.

[21] Appl. No.: 235,082

[22] Filed: Feb. 17, 1981

[51] Int. Cl.³ .............................................. G01N 27/04
[52] U.S. Cl. ......................................................... 73/23
[58] Field of Search .............. 75/23, 27 R; 324/71 SN; 340/634; 422/98, 88; 338/34

[56] References Cited

U.S. PATENT DOCUMENTS

| | | | |
|---|---|---|---|
| 3,479,257 | 11/1969 | Shaver | 340/632 |
| 3,865,550 | 2/1975 | Bott et al. | 73/23 |
| 4,030,340 | 6/1977 | Chang | 73/23 |

OTHER PUBLICATIONS

N. Ichinose et al., "Ceramic Oxide Semiconductor Elements for Detecting Components", *Ceramics*, 11 (3), pp. 203-211, 1976.

T. Seiyama et al., "Study on a Detector for Gaseous Components Using Semiconductive Thin Films," *Analytical Chemistry*, Vol. 38, No. 8, pp. 1069-1073, Jul. 1966.

*Primary Examiner*—Stephen A. Kreitman
*Attorney, Agent, or Firm*—Douglas D. Fekete

[57] ABSTRACT

In a preferred embodiment, the concentration of hydrogen or other reducing species in a gaseous sample is determined by measuring the electrical resistance of a zinc oxide thin film semiconductor having a gas-sensing surface exposed to the sample and carrying a thin spotted coating of a palladium-gold alloy. The palladium-gold alloy substantially improves the sensitivity of the resistance of the zinc oxide film to the presence of the reducing species.

6 Claims, 4 Drawing Figures

ZINC OXIDE THIN FILM SENSOR HAVING IMPROVED REDUCING GAS SENSITIVITY

BACKGROUND OF THE INVENTION

This invention relates to measuring the concentration of hydrogen or other reducing compound in a gaseous mixture using a zinc oxide thin film sensing element. More particularly, this invention relates to a zinc oxide thin film semiconductor having a gas-sensing surface that is partially covered by a platinum-gold alloy to substantially improve the responsiveness to reducing gas.

It has been reported that the electrical resistance of a semiconductive body of tin oxide or zinc oxide exposed to gas is sensitive to hydrogen or other reducing compounds in the gas. Also, it has been reported that the addition of palladium, platinum or gold enhances the sensitivity of the oxide body. For example, in U.S. Pat. No. 4,030,340 issued to Chang, June 21, 1977, a discontinuous coating of palladium or pallidum-gold alloy on a sputtered tin oxide thin film improved hydrogen sensitivity. Both coating materials performed substantially the same. In contrast, I have found that a zinc oxide thin film produced by sputtering from a sintered zinc oxide target does not respond to hydrogen. Neither is the film sensitized to hydrogen by a discontinuous coating of palladium metal or gold metal alone. Thus, it is totally unexpected that an alloy of the two metals would cause the film to be hydrogen sensitive.

Therefore, it is an object of this invention to provide a sensor and a method employing the sensor for detecting the presence of hydrogen, alkenes or other reducing species in a gaseous sample. The sensor comprises a sputtered zinc oxide thin film semiconductor whose electrical resistance alone is relatively insensitive of the reducing species. The sensor also comprises a gold-palladium alloy located so as to interact with the mixture and with the film in a manner that causes the film resistance to be affected by the reducing species.

It is a further object of this invention to provide a sensor and a method for using the sensor for detecting hydrogen or alkenes in a gaseous sample, which sensor comprises a thin film composed of a sputtered zinc oxide material and having islands of a palladium-gold alloy distributed on the surface. The palladium and gold synergistically cooperate to substantially improve the sensitivity of the zinc oxide resistance to the presence of the reducing species.

SUMMARY OF THE INVENTION

In a preferred embodiment, a sensor of this invention comprises a palladium-gold alloy deposited onto a gas-sensing surface of a thin film of a zinc oxide material. The zinc oxide thin film is prepared by sputtering from a zinc oxide target in an oxygen-argon atmosphere. The electroconductivity properties of the zinc oxide are such that the material alone is substantially unaffected by the presence of reducing species in ambient gas. The palladium-gold alloy is vapor deposited onto the film surface to form a discontinuous coating between 15 to 40 A° thick. By discontinuous it is meant that the coating is a matrix of microscopic alloy spots surrounded by uncovered zinc oxide. The alloy preferably consists of 30 to 70 weight percent gold and the balance palladium. After coating, the film is heated in air at 400° to 500° C. to stabilize the oxygen content of the zinc oxide.

The sensor of this invention is particularly useful for measuring hydrogen, although it is also suitable for measuring other gaseous reducing compounds. For sensing, the coated film surface is exposed to a gas sample while maintained at between 250° and 325° C. The electrical resistance of the zinc oxide material is measured across a path generally parallel to the surface of the film. The alloy interacts with the sample and the film in a manner that causes the resistance to decrease in logarithmic proportion to the concentration of hydrogen. Thus, the hydrogen concentration of an unknown sample can be determined by comparing the measured value with values obtained from known mixtures. The coated thin film is so sensitive that hydrogen may be accurately detected at levels of 100 ppm or less. This improvement in sensitivity cannot be explained based upon the behavior of either gold or palladium alone, since neither metal alone significantly affects hydrogen sensitivity. Rather, it is believed that the metals form a synergistic alloy that is unique for improving the hydrogen sensitivity of a sputtered zinc oxide thin film.

DETAILED DESCRIPTION OF THE INVENTION

Figure 1:
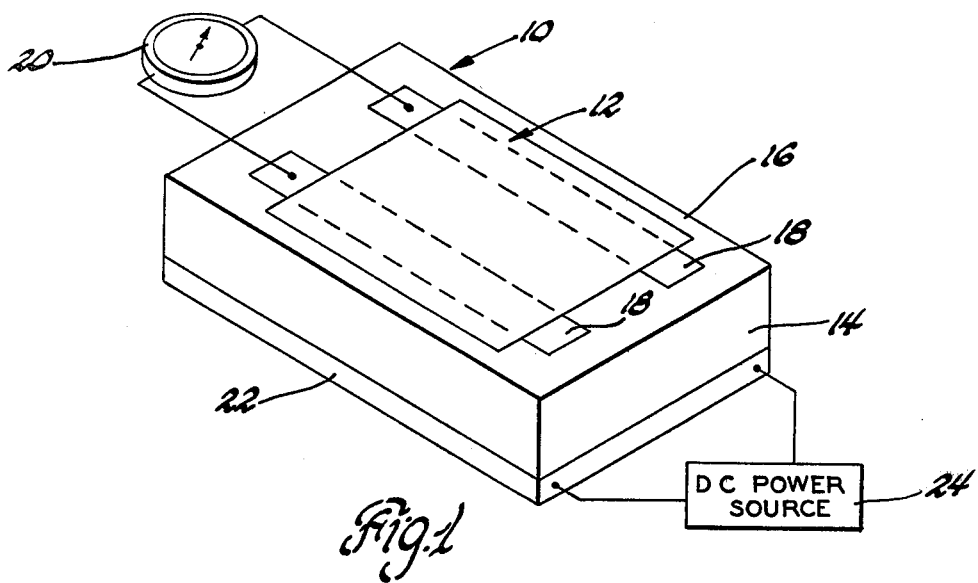
FIG. 1 is a perspective view of a coated solid state semiconductor sensor of this invention.

Referring to FIG. 1, a sensing element 10 comprising a semiconductive palladium-gold-coated zinc oxide thin film 12 is illustrated for measuring hydrogen or propylene in a gaseous mixture in accordance with a preferred embodiment of this invention. Sensor 10 comprises an alumina body 14 having dimensions of approximately 5 mm × 5 mm × 0.5 mm. Alumina is preferred because it is a good electrical insulator and has adequate thermal conduction to provide uniform heating of sensor 10. Body 14 has a first major surface 16 having a surface finish (the distance between the levels of the highest peak and the lowest valley) of approximately 400 A°. It is believed that the roughness of surface 16 increases the surface area of an applied film and enhances defects in the film to improve electroconductivity.

Two opposite, parallel gold-glass electrodes 18 having dimensions of 1 mm × 2 mm are applied to surface 16 using silk screen technology and fired. Electrodes 18 are spaced apart by approximately 1.5 mm. Electrodes 18 are connected to a low power ohmmeter 20 that measures the resistance of film 12 utilizing a substantially constant current of about one microampere. Maintaining sensor 10 at a constant temperature is critical to making accurate measurements. Since current passing through a resisting material generates heat, the use of a small constant current is preferred to avoid temperature fluctuations.

A resistance heater 22 is applied to body 14 opposite surface 16. The heater material displays a relatively constant and temperature-independent resistance at preferred gas-sensing temperatures. Adjacent corners of heater 22 are connected to a conventional DC power source 24. A chromel constantan thermocouple (not shown) is attached to the heater surface to provide a suitable signal for electrically controlling power source 24 and thereby maintaining sensor 10 at a desired temperature.

Figure 2:
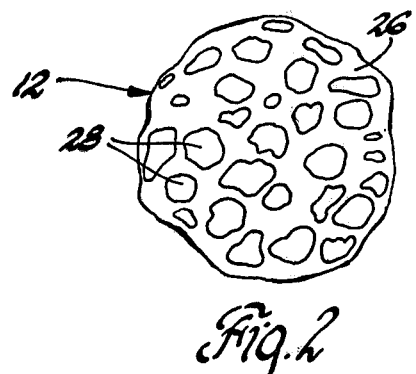
FIG. 2 is a magnified view of a portion of the surface of film 12 in FIG. 1.

As seen in FIG. 2, thin film 12 comprises a zinc oxide film 26 partially coated by spots 28 of palladium-gold alloy. Zinc oxide film 26 is applied to surface 16 over electrodes 18 and is continuous between the electrodes. Film 26 is deposited by RF sputtering from a sintered zinc oxide target in a low pressure oxygen-argon atmosphere. The target is prepared by pressing zinc oxide powder with a suitable organic binder and sintering to vaporize the binder and fuse the powder. A suitable mask is used to control deposition. Within a RF discharge plasma apparatus, substrate 14 is positioned on one electrode with surface 16 facing the target positioned upon the second electrode. The substrate-target distance is about 7.6 cm. The atmosphere contains approximately 8 millitorr partial pressure argon and approximately 2 millitorr partial pressure oxygen. The RF plasma is generated with a forward power of 400 watts and an accelerating voltage of 2.2 kilovolts (the target being cathodic). During sputtering, the temperature of substrate 14 does not exceed 200° C. Under these conditions, a suitable film is deposited after about 10 minutes. The product zinc oxide thin film 26 is approximately 1000 A° thick.

Alloy spots 28 are vapor deposited. In a vacuum chamber, film 26 is positioned facing a 0.5 mm diameter tungsten resistance heating wire. Wrapped around the tungsten wire is a thinner palladium-gold alloy wire about 0.125 mm in diameter. The preferred alloy consists of about 40 weight percent palladium and about 60 percent gold. A 50 amp current is passed through the tungsten wire to flash evaporate the alloy. The vaporized metals condense onto the surface of film 26. The large current heats the tungsten wire sufficiently fast to concurrently vaporize both metals, despite differences in their vaporization temperatures. Thus, the composition of spots 28 is essentially equivalent to the wire alloy.

The coated zinc oxide film is heated in air at between 400° to 500° C. for about 2 hours. This treatment stabilizes the oxygen content of the zinc oxide and suitably fixes the electroconductivity of the film for gas sensing. Also, the treatment may enhance a hydrogen-sensing relationship between the zinc oxide and the alloy.

In contrast to the white bare oxide film, the coated film appears metallic gray. When examined with an electron microscope, the coating is made up of a plurality of alloy spots 28 surrounded by uncovered zinc oxide 26, as seen in FIG. 2, It is estimated that the spots average about 25 A° in greatest dimension and cover about 70 percent of the geometric surface area. The coating thickness is measured with an in situ quartz thickness monitor during vapor deposition and is preferably about 35 A°. Auger spectroscopy shows that the alloy consists of about 40 percent palladium and 60 percent gold, the same as the wire, and that the spots are surrounded by bare zinc oxide.

Figure 3:
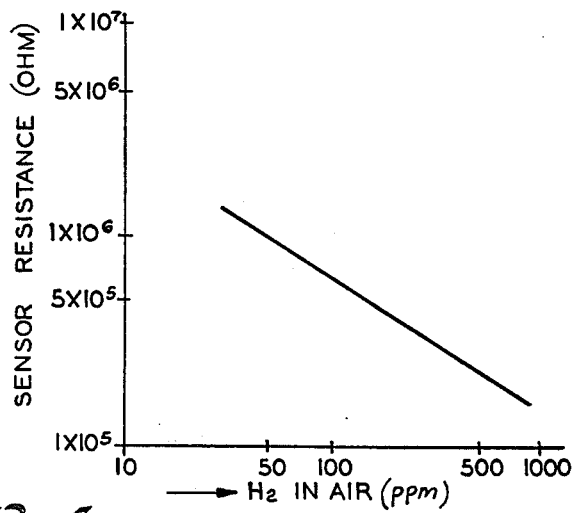
FIG. 3 is a graph on log-log coordinates of the electrical resistance of a coated thin film of this invention as a function of concentration of hydrogen ($H_2$) in air.

A sensor 10, prepared as described hereinabove, was tested by exposing to a gaseous sample in an airtight container. The samples consisted of room temperature air to which known hydrogen ($H_2$) additions were made. Heater 22 maintained the sensor temperature at about 300° C. The film resistance in the blank air sample (no $H_2$ added) was about $1.3 \times 10^7$ ohms. FIG. 3 shows the film resistance as a function of the hydrogen concentration, plotted on log-log coordinates. As seen, up to at least 1000 ppm, the logarithm of the sensor resistance decreases linearly with the logarithm of the hydrogen concentration. At 100 and 1000 ppm, the sensor resistance was $6.3 \times 10^5$ ohms and $1.5 \times 10^5$ ohms respectively, the latter value representing a hundred fold decrease from the blank resistance.

Figure 4:
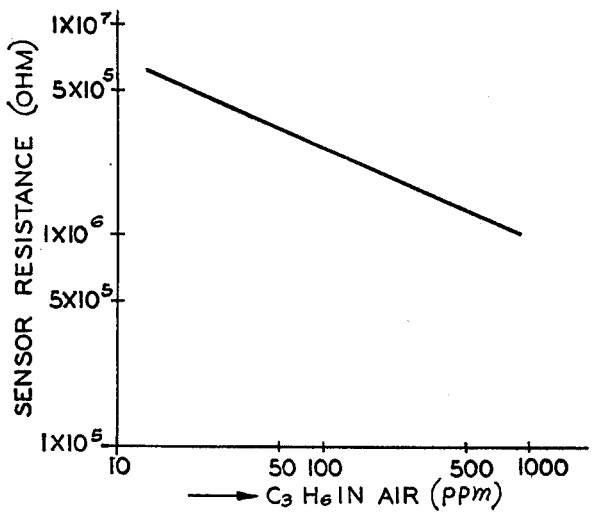
FIG. 4 is a graph on log-log coordinates of the electrical resistance of a coated thin film of this invention as a function of concentration of propylene ($C_3H_6$) in air.

A sensor was also tested to determine the response to propylene, another common gaseous reducing compound. The sensor was heated at 300° C. and exposed to room air samples containing known propylene ($C_3H_6$) additions. The results are depicted in FIG. 4. The film resistance in the blank air sample (no propylene) was about $1 \times 10^7$ ohms. The logarithm of the sensor resistance decreased linearly with the logarithm of the propylene concentration. An increase from 10 ppm to 100 ppm decreased the resistance from about $7 \times 10^6$ to about $2.5 \times 10^6$, about a threefold change. In contrast, the sensor resistance was not significantly affected by methane, which is not considered reducing.

Zinc oxide films having coatings of unalloyed palladium or unalloyed gold were not responsive to hydrogen or propylene. A sputtered zinc oxide film having a 35 A° discontinuous gold coating was exposed to an air sample. The resistance decreased from $5.6 \times 10^7$ ohms to only $3 \times 10^7$ ohms after the addition of 100 ppm hydrogen. An even smaller response was found to 100 ppm propylene. No significant resistance change was observed for either hydrogen or propylene with a sputtered zinc oxide film having a 31 A° palladium coating, as was the case with an uncoated zinc oxide film.

While I do not wish to be limited to any particular theory, it is believed that the sputtered and air-heat-treated zinc oxide has an oxygen to zinc ratio less than the ZnO stoichiometric ratio, that is, less than one. This oxygen deficiency results in defects in the zinc oxide crystalline structure that supply electrons for conduction through the crystal. Thus, zinc oxide is an N-type semiconductor. However, in contrast to other zinc oxide materials, the uncoated sputtered zinc oxide thin film is essentially nonresponsive to hydrogen or propylene. The role of the palladium-gold coating in enhancing sensitivity is not fully understood. One possibility is that alloy produces an excited hydrogen species that is itself chemisorbed onto the oxide surface or reacts with oxygen chemisorbed on the surface to alter the electron conduction properties of defects near the surface. Another possibility is that the reducing gas interacts with the alloy in a manner that affects underlying zinc oxide defects. However, the responsiveness of the alloy in contrast to the neat metals cannot be explained adequately.

Suitable reducing gas sensitivity is found for alloys consisting of about 10 to 90 weight percent gold and the balance palladium. However, below about 30 and above about 70 percent gold, the magnitude of the resistance change drops off. Thus, alloys containing 30 to 70 percent gold are preferred.

In the preferred embodiment, the coating is in intimate contact with the zinc oxide and covers a substantial portion of the surface while exposing sufficient zinc oxide for interaction with the gas. In general, suitable coatings cover less than about 70 percent of the zinc oxide geometric surface area. The geometric surface area is calculated from the linear dimensions of the film without regard for the roughness of the surface. More significantly, the preferred coating is discontinuous, that is, consisting of unconnected spots. A porous or continuous coating, although covering the same surface area, provides a preferential electron path that shorts the resistance measurement circuit across the film so that changes in the zinc oxide are not detected. In general, palladium-gold coatings less than 50 A° thick are discontinuous and suitable.

In the described embodiment, a zinc oxide film having a thickness of 1000 A° was deposited onto a substrate having a finish of about 400 A°. Film thickness and surface finish are interrelated parameters. Preferably, the film is sufficiently thick and the surface finish sufficiently smooth to produce a continuous film. However, the roughness of the substrate enhances lattice defects in the film. Thus, a substrate surface that is too smooth provides insufficient lattice defects. If the film is too thick, interactions with defects near the film surface do not have a measurable effect upon the overall film resistance. In general, substrates having surface finishes ranging between 300 to 4000 A° are suitable for use with zinc oxide film ranging between 600 and 10,000 A°.

Materials other than those mentioned above may be used to manufacture the substrate and the electrodes without significantly affecting the performance of the coated zinc oxide thin film. For example, other inert, refractory materials, such as steatite, are good electrical insulators and form suitable sensor bodies. Any good electrical conductor may be used for the electrodes. The heater need not be attached to the sensor. Attaching the heater as in the preferred embodiment permits the sensor to be maintained at a desired temperature without heating the entire sample. It has been found that the most accurate readings are obtained by operating the sensor between about 250° to 325° C., preferably between 270° to 300° C. Operated above that temperature range, the sensor responds faster, but typically overshoots. When the sensor is operated below that range, a slow response is obtained that typically represents too low a concentration.

Although this invention has been described in terms of certain embodiments thereof, it is not intended that it be limited to the above description but rather only to the extent set forth in the claims that follow.

The embodiments of the invention in which an exclusive property or privilege is claimed are defined as follows:

1. A device for detecting a gaseous reducing species comprising
    a thin film semiconductor comprising a continuous sputtered zinc oxide material and having a gas-sensing surface comprising discrete microscopic alloy bodies surrounded by the zinc oxide, said film being adapted for measuring the electrical resistance of the zinc oxide across the film, said bodies being composed of an effective palladium and gold alloy for substantially enhancing the sensitivity of the resistance of the zinc oxide to the reducing species.

2. A device for sensing a reducing species in a gaseous sample comprising
    a thin film having a gas-sensing surface and composed of a sputtered oxygen-deficient zinc oxide material,
    a thin alloy coating on the film surface and consisting of 10 to 90 weight percent gold and the balance palladium, said coating having a thickness between about 15 to 40 A° and comprising microscopic spots separated by exposed zinc oxide in a suitably discontinuous pattern to allow measurement across the film of the electrical resistance of the zinc oxide material,
    means for maintaining the film at a temperature between 250° and 325° C., and
    electrode means contacting the film for measuring the electrical resistance across the film, whereby the resistance provides a measure of the reducing gas concentration in the sample.

3. A sensor for measuring the concentration of a reducing compound selected from the group consisting of hydrogen and alkenes in a gaseous sample, said device comprising
    an inert substrate,
    a thin film on said substrate and composed of a sputtered and air-heat-treated zinc oxide material whose electrical conductivity is substantially insensitive by itself to the reducing species, said film having a thickness between about 600 to 10,000 A°,
    a vapor deposited palladium-gold alloy coating on a surface of the film for sensitizing the electrical resistance of the zinc oxide to the reducing compound, said coating comprising discrete microscopic alloy spots surrounded by exposed zinc oxide and consisting essentially of 30 to 70 weight percent gold and the balance palladium,
    heating means for maintaining the coated film at a temperature between 250° and 325° C., and
    at least two electrodes contacting the film and spaced apart for measuring the electrical resistance across the film, whereby the measured resistance is indicative of the concentration of reducing gas in the sample.

4. A method for detecting the presence of a reducing species in a gaseous sample comprising measuring the electrical resistance of a thin film semiconductor formed of oxygen-deficient zinc oxide material and having a surface exposed to the sample, said surface also comprising microscopic bodies surrounded by exposed zinc oxide and composed of an effective palladium and gold alloy for sensitizing the resistance of the zinc oxide to the reducing species, said film having a predetermined resistance to a like sample free of reducing species, whereby the presence of reducing species in the sample is indicated by a substantial decrease in the measured resistance below the predetermined value.

5. A method for analyzing a gaseous sample for the presence of a reducing species comprising
    exposing a surface of a thin film composed of a sputtered and air-heat-treated zinc oxide material to the sample, said surface comprising microscopic palladium-gold alloy spots surrounded by zinc oxide, said alloy comprising between about 30 to 70 weight percent gold and the balance palladium and sensitizing the electrical resistance of the zinc oxide material to the presence of the reducing species,
    maintaining the film at a temperature between 250° and 325° C.,
    measuring the electrical resistance of the zinc oxide film while exposed to the sample, whereby the measured resistance provides a measure of the reducing species in the sample.

6. A method for analyzing a gaseous sample for a reducing compound selected from the group consisting of hydrogen and alkenes, said method comprising
    sputtering a zinc oxide material from a zinc oxide target onto an inert substrate to form thereon a continuous thin film that is between about 600 to 10,000 A° thick, flash vapor depositing a palladium-gold alloy onto the zinc oxide film to form a coating between about 15 to 40 A° thick, said coating comprising microscopic alloy spots surrounded by uncoated zinc oxide, said alloy consisting of 30 to 70 weight percent gold and the balance palladium, heat treating the coated film in air for a sufficient time to stabilize the oxygen content of the zinc oxide at an oxygen-to-zinc ratio less than a stoichiometric one, exposing the coated film to said mixture whereupon reducing compound interacts with the alloy and the zinc oxide in a manner that affects the resistance of the zinc oxide film, heating the film to between about 250° and 325° C. while exposed to the sample, measuring the electrical resistance of the zinc oxide material while the film is exposed to the sample, said resistance being measured across a path generally parallel to the coated film surface, and comparing the measured resistance to similar resistance values for known gaseous compositions to determine the concentration of the compound in the mixture.

* * * * *